(12) United States Patent
Kates

(10) Patent No.: US 7,552,730 B2
(45) Date of Patent: Jun. 30, 2009

(54) METHOD AND APPARATUS FOR DEFENDING AGAINST NASO-PHARYNGEAL VIRAL ATTACKS

(76) Inventor: Lawrence Kates, P.O. Box 2400, Santa Monica, CA (US) 90407

( * ) Notice: Subject to any disclaimer, the term of this patent is extended or adjusted under 35 U.S.C. 154(b) by 0 days.

(21) Appl. No.: 11/062,175

(22) Filed: Feb. 22, 2005

(65) Prior Publication Data

US 2005/0166919 A1    Aug. 4, 2005

Related U.S. Application Data

(62) Division of application No. 10/445,140, filed on May 23, 2003, now Pat. No. 7,073,500.

(51) Int. Cl.
*A61M 16/00* (2006.01)
*A61M 15/00* (2006.01)

(52) U.S. Cl. .............. 128/203.26; 128/203.16; 128/203.17; 128/200.14; 128/204.18

(58) Field of Classification Search ........... 128/200.11, 128/200.14, 200.24, 203.12, 203.16, 203.17, 128/203.26, 203.27, 204.18, 204.21, 204.14, 128/204.17; 239/102.2; 261/128
See application file for complete search history.

(56) References Cited

U.S. PATENT DOCUMENTS

| | | | |
|---|---|---|---|
| 3,291,122 A | 12/1966 | Carl-Gunnar et al. | |
| 4,369,777 A | 1/1983 | Lwoff et al. | |
| 4,401,114 A | 8/1983 | Lwoff et al. | |
| 4,523,589 A | 6/1985 | Krauser | |
| 4,681,099 A | 7/1987 | Sato et al. | |
| 4,699,136 A | 10/1987 | Krauser | |
| 4,776,990 A * | 10/1988 | Verity ..................... 261/128 |
| 4,805,614 A * | 2/1989 | Lerner .................. 128/203.17 |
| 4,955,372 A | 9/1990 | Blackmer et al. | |
| 5,038,769 A | 8/1991 | Krauser | |
| 6,152,130 A * | 11/2000 | Abrams et al. ......... 128/204.21 |
| 6,247,470 B1 | 6/2001 | Ketchedjian | |
| 6,435,180 B1 * | 8/2002 | Hewson et al. ......... 128/204.18 |

(Continued)

FOREIGN PATENT DOCUMENTS

DE       3049244 A       7/1982

(Continued)

OTHER PUBLICATIONS

Office Action dated Apr. 19, 2005 from Related U.S. Appl. No. 10/445,140.

(Continued)

*Primary Examiner*—Justine R Yu
*Assistant Examiner*—Annette F Dixon
(74) *Attorney, Agent, or Firm*—Knobbe, Martens, Olson & Bear, LLP

(57) ABSTRACT

An apparatus is disclosed for practicing a method of treating viruses in the nasal mucosa. Vapor is generated, heated and delivered to the nasal mucosa in intermittent bursts, timed to coincide with inhalation. Control circuits are provided to maintain the temperature of the vapor at the point of delivery at a level greater than that necessary to kill viruses in the nasal mucosa. Timing circuits can synchronize the vapor delivery with a breathing cycle with heated vapor being supplied during inhalation and blocked during exhalation. Other circuits terminate operation when liquid is insufficient or after a predetermined timed interval.

8 Claims, 7 Drawing Sheets

U.S. PATENT DOCUMENTS

| | | | |
|---|---|---|---|
| 6,729,327 B2 | 5/2004 | McFarland | |
| 6,951,218 B2 * | 10/2005 | Gradon et al. | 128/205.25 |
| 7,073,500 B2 | 7/2006 | Kates | |
| 7,096,867 B2 * | 8/2006 | Smith et al. | 128/207.11 |
| 2004/0231668 A1 | 11/2004 | Kates | |
| 2006/0231095 A1 | 10/2006 | Kates | |

FOREIGN PATENT DOCUMENTS

| | | |
|---|---|---|
| DE | 3707228 A | 9/1987 |
| DE | 19953317 C1 | 2/2001 |
| EP | 0983103 | 4/2002 |
| WO | WO 03-059425 A | 7/2003 |

OTHER PUBLICATIONS

Office Action dated Oct. 19, 2005 from Related U.S. Appl. No. 10/445,140.

Office Action dated Apr. 4, 2006 from Related Appl. No. 10/445,140.

Notice of Allowance dated May 2, 2006 from Related Appl. No. 10/445,140.

Yerushalmi et al., "Treatment of Perennial Allergic Rhinitis by Local Hyperthermia," Proceedings of the National Academy of Science, vol. 79, pp. 4768-4769, Aug. 1982.

Forstall et al., "Effect of Inhaling Heated Vapor on Symptoms of the Common Cold," Journal of the American Medical Association, vol. 271, No. 14, pp. 1109-1111, Apr. 13, 1994.

* cited by examiner

METHOD AND APPARATUS FOR DEFENDING AGAINST NASO-PHARYNGEAL VIRAL ATTACKS

This is a divisional application of my non-provisional application for letters patent, Ser. No. 10/445,140, filed May 23, 2003 now U.S. Pat. No. 7,073,500.

BACKGROUND OF THE INVENTION

1. Field of the Invention

The present invention relates to a method for relieving the symptoms of viral attacks to the naso-pharyngeal mucosa and an apparatus for providing such relief.

2. Description of the Related Art

It has been known for some time that heat applied to the nasal passages can provide relief to persons suffering from rhinitis or other attacks to the naso-pharyngeal mucosa, whether due to allergic conditions, the common cold, or any other factor. Early researchers, such as A. Yerushalmi, et al, published reports of their activities in the Proceedings of the National Academy of Science 79, 4766-4769, in August 1982. Earlier, A. Yerushalmi and A. Lwoff published in C.R. Acad. Sc. Paris, t. 291.

However, these findings were disputed in a paper, "Effect of Inhaling Heated Vapor on Symptoms of the Common Cold" published by Gregory J Forstall, MD, et al. in the Journal of the American Medical Association ("JAMA") on Apr. 13, 1994 at Vol 271, No. 14, pp. 1109-11. The conclusion of these writers was that " . . . steam inhalation treatment had no beneficial effect on the cold symptoms of our volunteers." These conclusions are somewhat at variance with anecdotal reports of relief after ingesting hot chicken soup or using a steam inhaler.

Several patents have taught apparatus to deliver heated and moistened vapor to the nasal cavities to provide relief from symptoms of what was believed to be the common cold or rhinitis. In U.S. Pat. Nos. 4,369,777 and 4,401,114, Lwoff et al taught a method and apparatus for treating the common cold using a stream of heated, humidified air under pressure which was delivered to the nasal mucosa without inhalation. Further, the outlet stream was not pressurized and the kinetic energy of the heated, humidified stream was sufficient to carry the stream some 3 cm into the nasal passages.

In a series of related patents issuing between 1985 and 1991, Krauser taught a method and apparatus for treating ailments, U.S. Pat. Nos. 4,523,589; 4,699,136 and 5,038,769. Krauser supplied a vaporized pharmaceutical or medicament to a heated air stream His theory was that the heated stream, when combined with a microbicide such as hexylresorcinol or povidone-iodine could eliminate cold symptoms within twelve to thirty six hours. The heated air may be delivered separately from the microbicide, which allows use as an inhaler without the heated air stream. A recommended procedure was to apply heated air for five, approximately 15 second intervals separated by 5 second rest intervals after which the microbicidal spray was applied in three quick bursts. This treatment cycle was to be repeated three to four times per day.

In the patent to Verity, U.S. Pat. No. 4,776,990, an improved nebulizer was taught that utilized an ultrasonic generator in combination with a high velocity jet of heated gas to produce a stream of heated vapor which is than applied to nasal passages. Verity, too recommends applying the stream without the need for inhalation. Further, Verity believed that temperatures above 43°_C. were more effective.

Yet another device was disclosed in the patent to Lerner, U.S. Pat. No. 4,805,614. Lerner used a steam generator in combination with a air stream. By selecting the diameter of the conduit for delivering the output stream in relation to the length of the conduit, a homogeneous stream can be produced at a desired temperature around 47°_C. However, no particular treatment protocol is suggested so it is to be assumed that Lerner intends to use the procedures outlined in other prior art patents and publications.

SUMMARY OF THE INVENTION

According to the present invention, it has been determined that while the earlier methods suggested in the prior art may have had the potential for success, there was a failure to recognize the problem of compliance. Continuous exposure to heated vapors eventually produces some degree of discomfort and therefore a reluctance to suffer the treatment for a period sufficient to produce the desired results.

Approximately one hour, especially at the onset of first cold symptoms, is believed to be most effective. In order to achieve compliance, it was determined that heated moisturized vapor should be delivered to the nasal passages intermittently, during inhalation and not necessarily at other times. It was also determined that the treatment would not be adversely affected if the user exhaled through the nose.

It is believed that rhino viruses and many other viruses and bacteria cannot survive at the normal human body temperature of 98.6° F. or slightly higher. Normally, the temperature of the nasal mucosa, being exposed to the ambient air temperature, is 3 or 4 degrees less, averaging about 94° F. which can be a hospitable environment for virus replication and bacterial growth. It is therefore a goal of the present invention, and the researchers of the prior art, to maintain a nasal temperature of 99° or as high as the comfort level of the user will permit for a period long enough to destroy the rhinovirus, other viruses and some bacteria. According to the present invention, it is believed that period should be at least an hour although clinical trials may determine that lesser or greater periods may be most efficacious.

It has been found that exposure to a heated air stream for an interval approximately equal to the inhalation phase of a breathing cycle, if continued for an hour, can be effective in warding off colds, if done early enough in the incubation period, and in providing palliative relief, if not. For the rest of the breathing cycle, the nose is permitted to rest. This should not adversely impact the treatment inasmuch as the exhaled air will be at the core temperature of the body, if not higher.

To facilitate practice of the method of the present invention, a specialized heated vapor delivery system has been created which includes a base unit provided with a fluid reservoir and associated atomizer, an air pump and electronic control and timing circuits. A tube or conduit, which is adapted to carry air and vapor, conveys the vapor and the air as a heated mist to a dispenser head that delivers the mist.

The mist, as it is produced, is initially directed against a sensor that is adjacent a heating coil that heats the mist to a temperature sufficiently above 110° F. so that the mist exiting the system and entering the nose of the user is at a temperature adequate to kill the hostile viruses or bacteria in the nose. In the present invention, water is the liquid of choice for the vapor or mist.

In the preferred embodiment, the dispensing head is attached to a head set, much as a boom microphone, commonly found on hands free telephones. The dispensing head is placed in close proximity to the nose of the user and, in normal operation, dispenses a stream of vapor heated to approximately 110° F., although a range of temperatures adequate to provide a hostile environment to viruses and bacteria may be provided. The electronic circuits in the base unit control the atomizer and a solenoid valve in the head set to operate on an intermittent basis, providing "pulses" of heated vapor at regular, selectable intervals.

Typically, a pulse will be of a duration of between 500 and 750 milliseconds and will be provided at a frequency of 1000-3000 milliseconds. although a wider range of pulse durations and frequencies are provided. The pulses may be square, ramped or sinusoidal, depending upon the choice of the circuit designer. The electronic circuits can also regulate the flow of air to control the temperature of the exiting stream of heated, moist vapor although, in the preferred embodiment, the heater is cycled on and off to maintain the temperature of the vapor.

In an alternative embodiment, a specialized heated vapor delivery system has been created which includes a base unit provided with a fluid reservoir and associated pump, an air pump and electronic control and timing circuits. A tube or conduit, which is adapted to carry air and liquid separately, conveys the fluid and the air, separately to a dispenser head in which the air and fluid is combined in a venturi that produces a mist. The mist is directed against a screen that is maintained at a temperature above the boiling point of water. In the preferred embodiment, water is the liquid of choice and will be converted to steam as the mist passes through the screen.

In this embodiment, the dispensing head is attached to a head set, much as a boom microphone, commonly found on hands free telephones. The dispensing head is placed in close proximity to the nose of the user and, in normal operation, dispenses a stream of steam vapor heated to approximately 110° F., although the controls will allow a range of temperatures. The electronic circuits in the base unit control the liquid pump to operate on an intermittent basis, providing "pulses" of heated vapor at regular, selectable intervals. Typically, a pulse will be of a duration of between 500 and 750 milliseconds and will be provided at a frequency of 3-5 seconds, although a wider range of pulse durations and frequencies are provided. The electronic circuits can also regulate the flow of air to control the temperature of the exiting stream of heated, moist vapor.

In alternative embodiments, a more complex apparatus can be employed in which steam is generated within the base unit and is released to the user in controlled bursts using a solenoid valve. The frequency and duration of the bursts is then controlled solely be the valve. Temperature sensors are provided to monitor the output stream to assure that the predetermined temperatures at the exit point are maintained within a narrow range of the desired optimum temperature.

In yet other embodiments, a vacuum unit may be employed to scavenge steam and heated moistened air from the area of the nose at times other than the inhalation cycle to prevent irritation or undue heating.

The novel features which are characteristic of the invention, both as to structure and method of operation thereof, together with further objects and advantages thereof, will be understood from the following description, considered in connection with the accompanying drawings, in which the preferred embodiment of the invention is illustrated by way of example. It is to be expressly understood, however, that the drawings are for the purpose of illustration and description only, and they are not intended as a definition of the limits of the invention.

DESCRIPTION OF THE PREFERRED EMBODIMENTS

Figure 1:
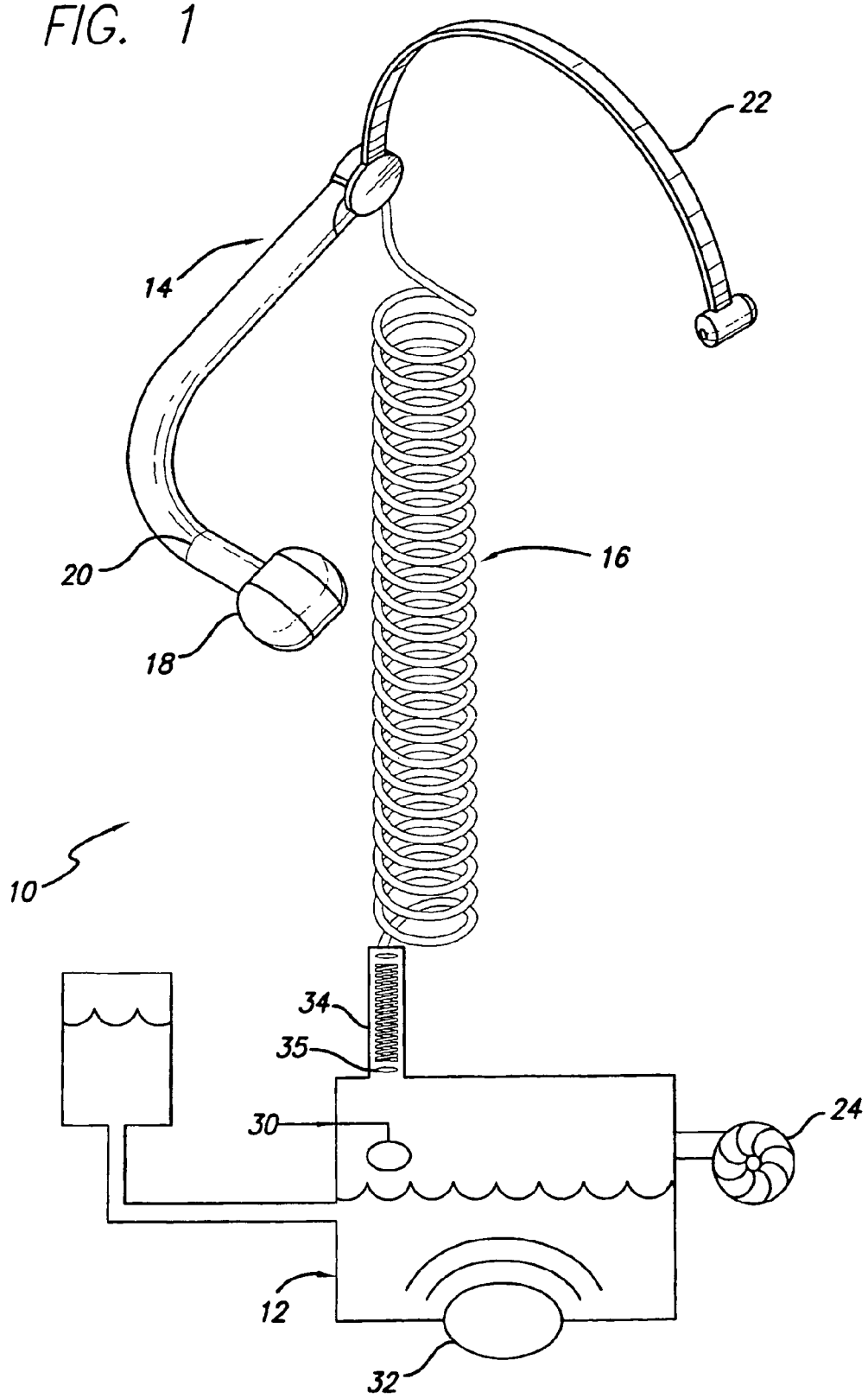
FIG. 1 is a perspective view of an heated mist dispenser according to a preferred embodiment of the invention.

Turning first to FIG. 1, there is shown, in perspective, a treatment delivery apparatus 10 according to the present invention. The apparatus 10 includes a base unit 12, a dispensing unit 14 and a conduit 16 connecting the two electrically and with a supply of fluid, preferably a heated water mist. Electrical power is supplied through a power cord and transformer (not shown) so that the apparatus operates at a relatively safe low voltage of approximately fifteen (15) volts., although lower voltages are possible.

As shown, the dispensing unit 14 includes a dispensing head 18 that is connected to the conduit 16. The dispensing head 18 is supported by a boom element 20 which is attached to a u-shaped head piece 22. The head piece 22 is flexible and is intended to be supported by the user's head. The boom element 20 is adjustable so that the dispensing head 18 can be conveniently positioned adjacent the user's nose. This configuration assures that the vapors emanating from the dispensing head 18 will be directed into the nasal cavities to affect the nasal mucosa.

The base unit 12 includes an air pump 24 which continually operates to provide a pressurized air stream to the conduit 16. The base unit includes a reservoir 26 which is sized to hold sufficient liquid for approximately sixty (60) minutes of continuous operation. An external tank 28 contains additional fluid and is intended to accept additional liquid as necessary. A float switch 30 is provided in the reservoir 26 so that an alarm can be given when the fluid level is low. The switch 30 can also terminate operation if there is insufficient liquid to operate safely.

An atomizer element 32, which may be an acoustic ultrasound generator, creates a liquid mist or fog above the surface of the liquid which is entrained in the air stream provided by the pump 24. A heater coil 34 is positioned in the base unit exit port to heat the vapor mist prior to its entry into the conduit 14. A heater temperature sensor 35 placed upstream from the heater coil 34 measures the temperatures of the vapor moving up the conduit 16.

In operation, the pump 24 provides a stream of air which captures the atomized liquid in the form of a fog or mist and carries the liquid/air mixture through the heater 34 which elevates the temperature of the mixture to a level sufficient to provide a stream of heated mist to the dispensing head at approximately 110° F. To a certain extent, the temperature of the emerging stream is regulated by operating the heater coil 34 intermittently. The thermal mass of the heater coil 34 is such that it will cool gradually when the power is off and can be reheated by applying power. The temperature of the vapor will then fluctuate between a maximum, which when detected by the sensor 35 causes the power to be interrupted, and a minimum, which, when detected, causes the power to be restored.

In alternative embodiments, the temperature of the heater coil 34 can remain constant and vapor temperature can be regulated by varying the speed of the pump 24. When the vapor temperature reaches a desired maximum value, the pump 24 velocity can be increased, thereby shortening the time of the vapor in the heating coil 34. When the temperature of the vapor drops to a predetermined minimum, the pump 24 velocity can be decreased, lengthening the transit time of the vapor through the heating coil 34.

Figure 2:
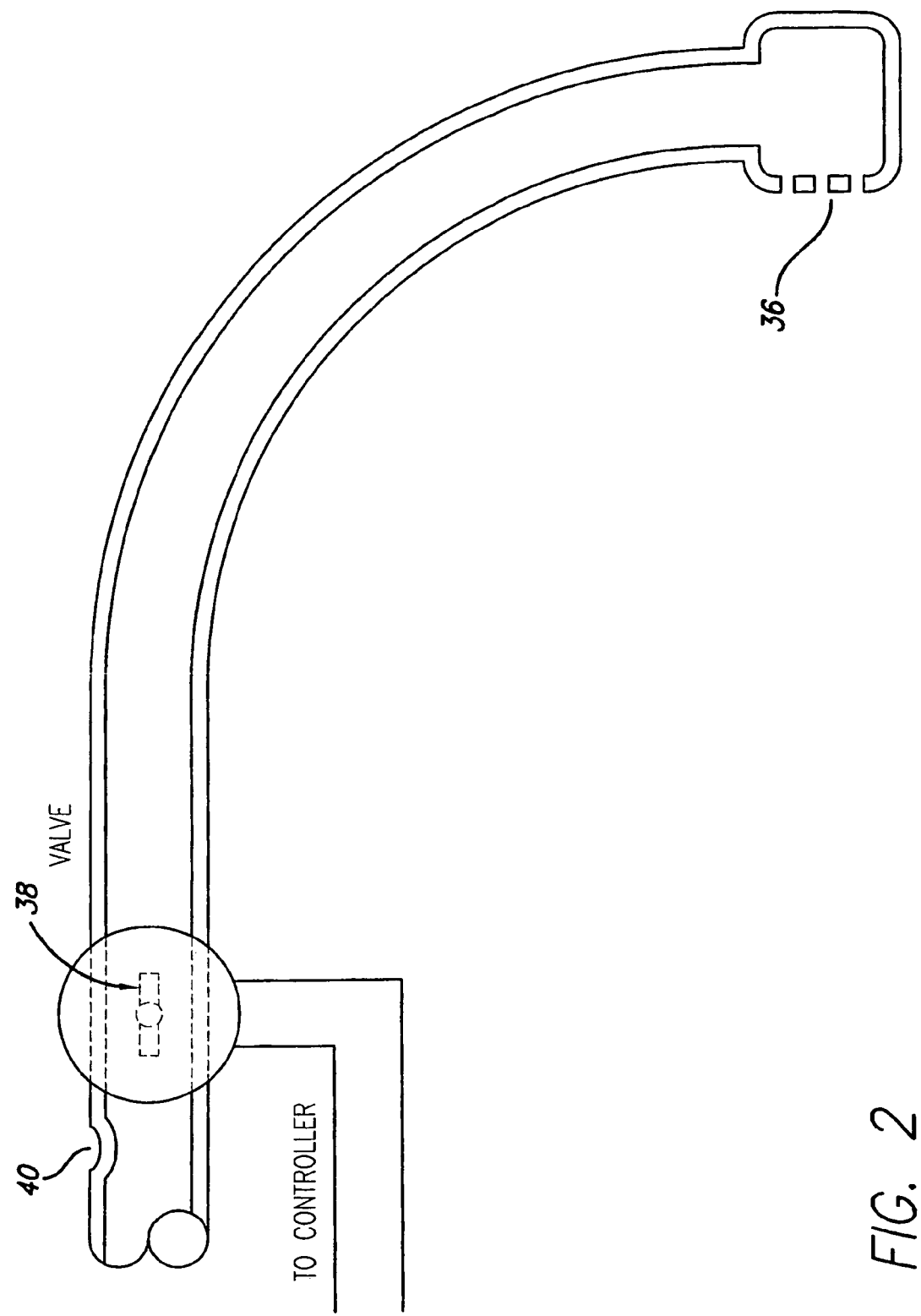
FIG. 2, is an idealized side view of an embodiment of the dispenser unit and the head piece assembly showing the valve in phantom.
Figure 3:
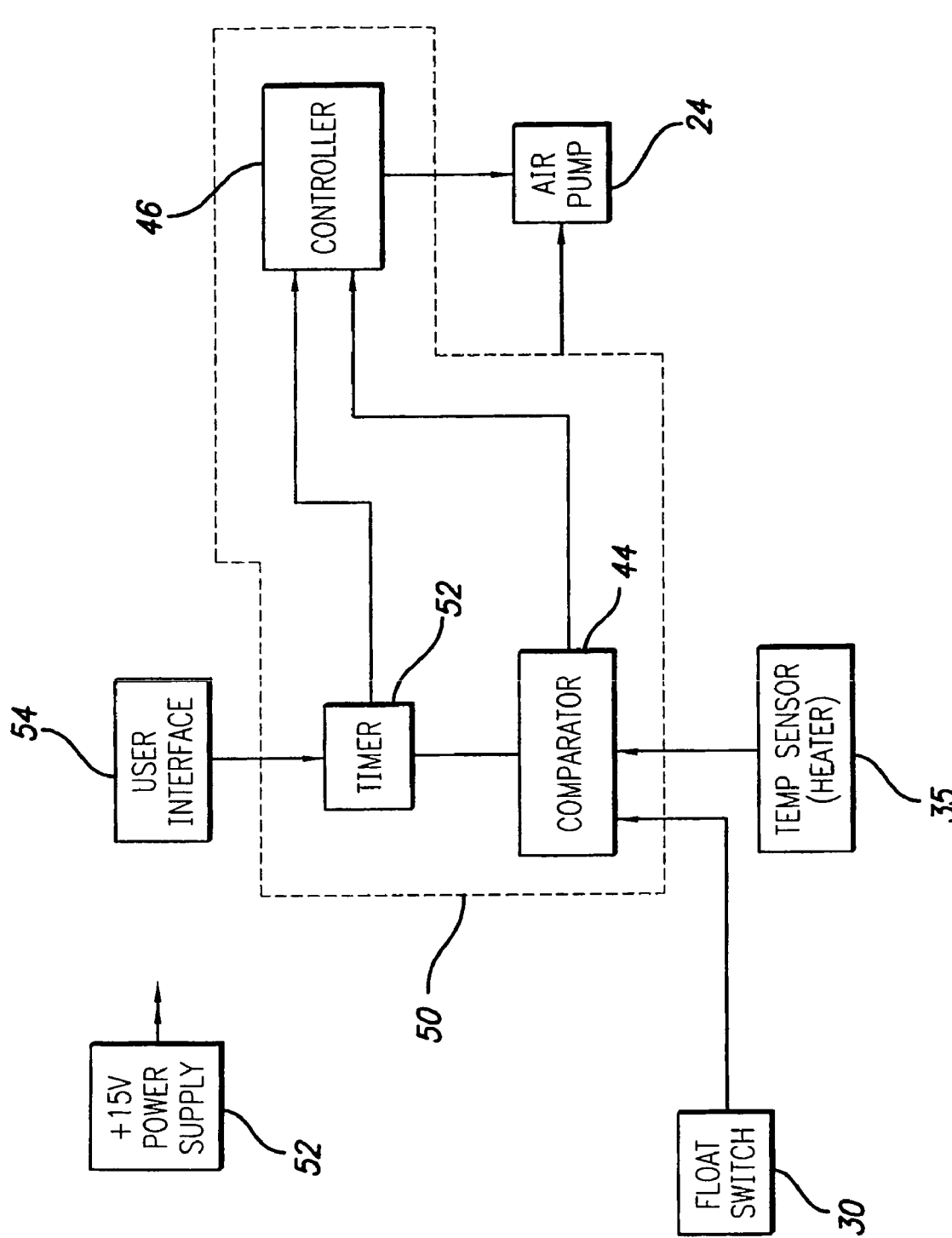
FIG. 3 is a block diagram of the control circuit elements of the mist dispenser of FIG. 1.
Figure 4:
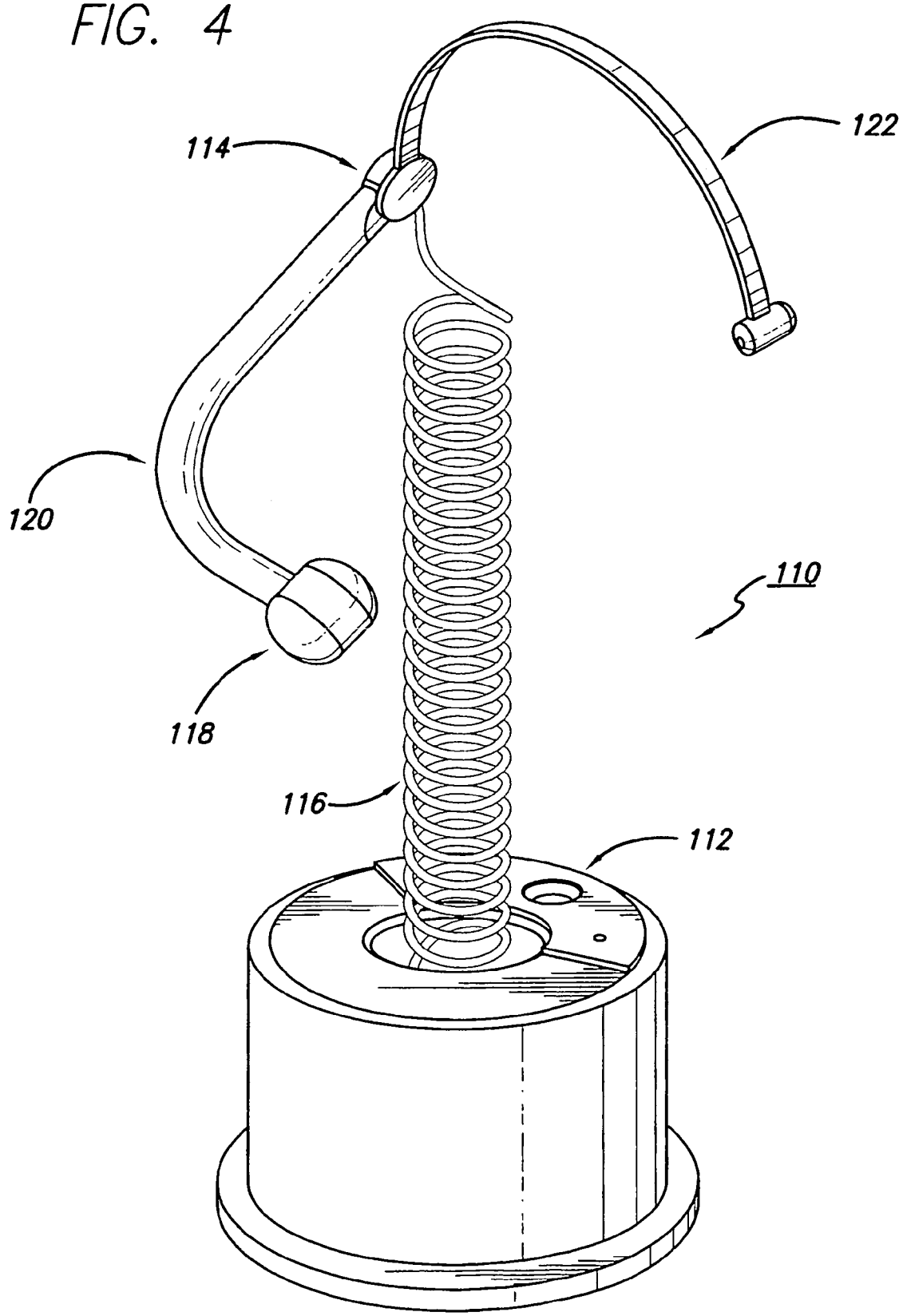
FIG. 4 is a perspective view of an heated mist dispenser according to a first alternative embodiment of the invention.
Figure 5:
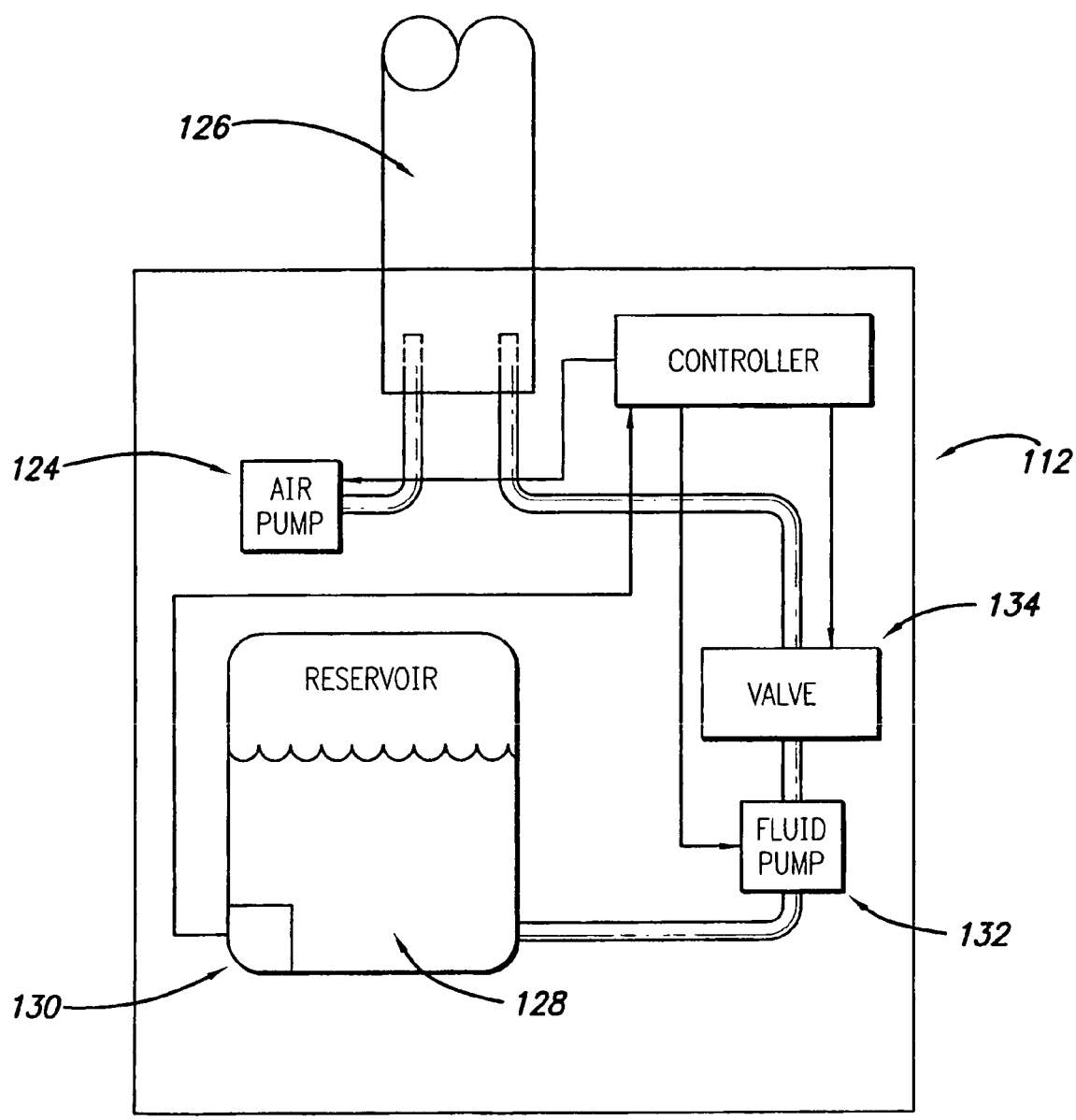
FIG. 5 is a block diagram of the components of the base unit of FIG. 4.
Figure 6:
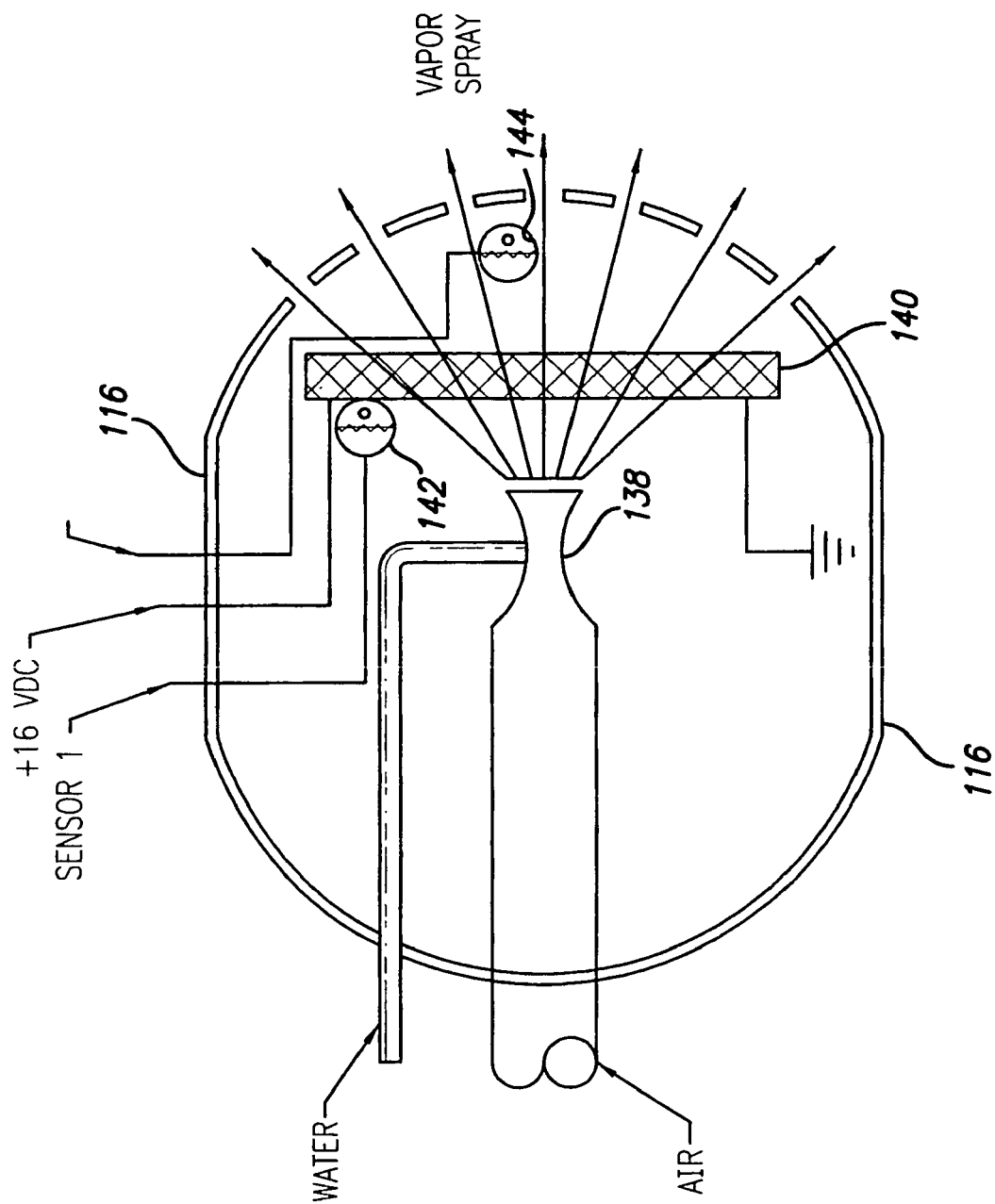
FIG. 6 is a side sectional view of a dispenser unit for the embodiment of FIG. 4.
Figure 7:
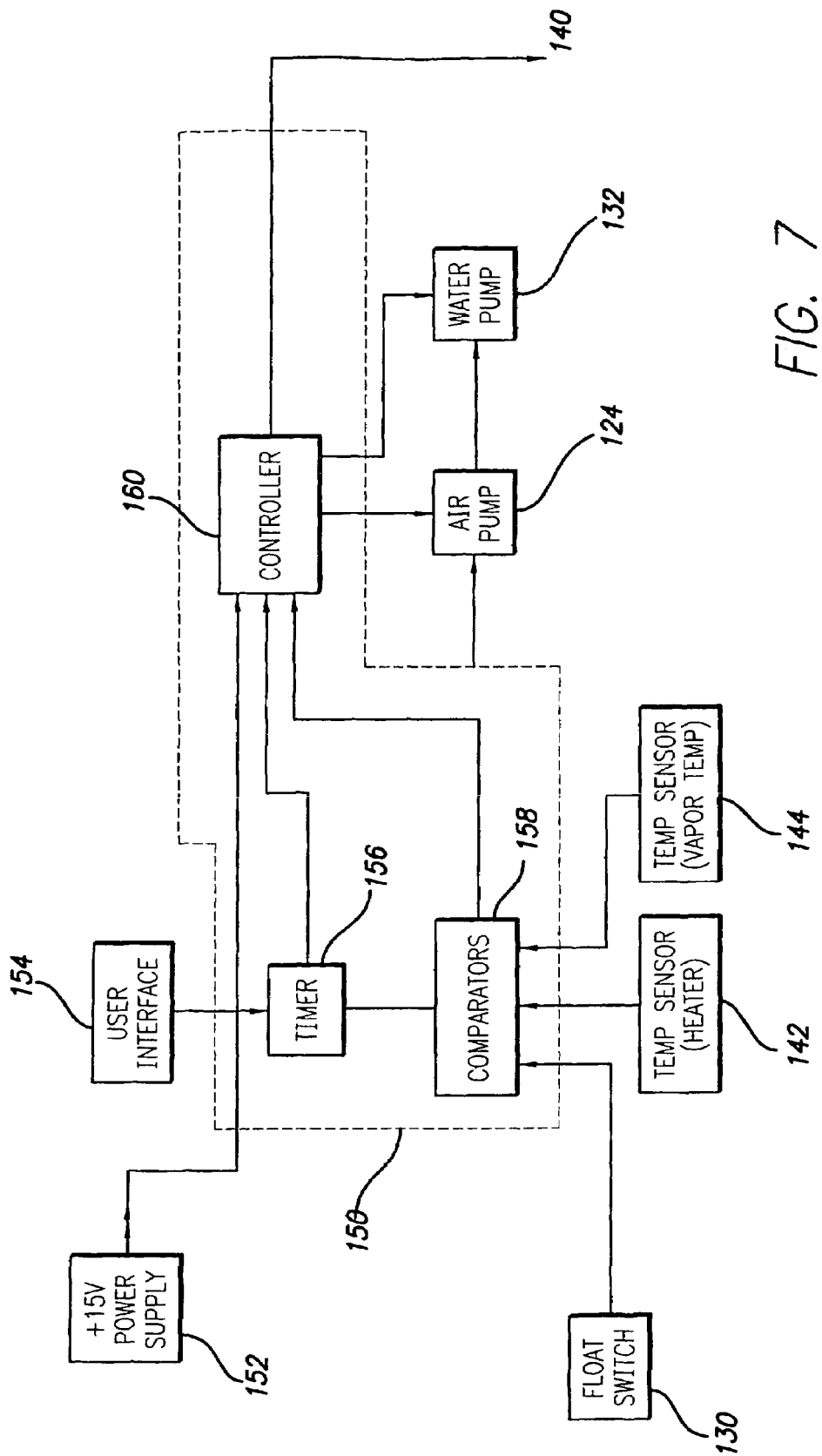
FIG. 7 is a block diagram of the control circuit elements for the embodiment of FIG. 4.

The components of the dispenser head 18 are shown in side section in FIG. 2. The head 18 includes a dispensing tip 36 at the outward end, intended to be adjacent the user's nose. A valve 38 and a vent 40 are located at the inner end adjacent the conduit 16 where the heated vapor enters the dispensing unit 14. The valve 38 is operated intermittently, to synchronize with the user's breathing, being held open during an inhalation and closed during exhalation.

When the valve 38 is opened, the vapor is directed to the dispensing tip 36. To assure free flow, the vent 40 brings in ambient air in a venturi flow effect. When the valve 38 is closed, the vapor is exhausted to the exterior through the vent 40, so that the flow from the base is unimpeded. When the valve 38 is closed, the heated vapor is shunted to the open vent and away from the face of the user.

FIG. 3 is a block electrical diagram of the circuits controlling the operation of the present invention. The float switch 30 and the heater temperature sensor 35 of FIG. 1 are connected to a comparator circuit 44, which compares each of the applied inputs to a preset values and provides a signal to a controller circuit 46, signaling if either of the sensors has detected a parameter that departed from desired values. For example, if the float switch 30 signals insufficient liquid in the reservoir 26, the controller circuits 46 could provide audible alarms and disable the heater 34, the atomizer 32 and the pump 24.

Similarly, if the vapor temperature at the heater coil 24 is less than desired, the controller circuits 46 could turn on the heater 34 until the temperature of the vapor reached the desired level. If the vapor temperature exceeds desired levels, the controller circuits 46 could reduce the temperature of the heater 34 by stopping the current to it.

Turning next to FIG. 4, there is shown, in perspective, a an alternative embodiment of a treatment delivery apparatus 110 according to the present invention. The apparatus 110 includes a base unit 112, a dispensing unit 114 and a conduit 116 connecting the two electrically and with a supply of fluid, preferably water, and gas, preferably air. Electrical power is supplied through a power cord and transformer (not shown) so that the apparatus operates at a relatively safe low voltage of approximately fifteen (15) volts., although lower voltages are possible.

As shown, the dispensing unit 114 includes a dispensing head 118 that is connected to the conduit 116. The dispensing head 118 is supported by a boom element 120 which is attached to a u-shaped head piece 122. The head piece 122 is flexible and is intended to be supported by the user's head. The boom element 120 is adjustable so that the dispensing head 118 can be conveniently positioned adjacent the user's nose. This configuration assures that the steam vapors emanating from the dispensing head 118 will be directed into the nasal cavities to affect the nasal mucosa.

In FIG. 5, the components of base unit 112 are shown in block diagrammatic form. The base unit 112 includes an air pump 124 which continually operates to provide a pressurized air stream to the air carrying portion 126 of the conduit 116. A fluid reservoir 128, which is sized to hold sufficient liquid for approximately ninety (90) minutes of continuous operation, is also housed in the base unit 112. A float switch 130 is provided so that an alarm can be given when the fluid level is low. The switch 130 can also terminate operation if there is insufficient liquid to operate safely. A fluid pump unit 132 draws fluid from the reservoir 128 and delivers it, though a unidirectional valve 134, to the liquid carrying portion 136 of the conduit 116.

In operation, the liquid pump unit 132 is powered by the output of the controller circuits and is operated intermittently. Initially, the pump unit 132 operates to fill the liquid carrying portion 130 of the conduit 116 and dispenses the first increment of fluid. Thereafter, the conduit 116 remains filled with fluid so that each operation of the pump 132 thereafter, supplies a predetermined liquid increment to the dispenser unit 114.

The components of the dispenser head 18 are shown in FIG. 6. A venturi unit 138 is coupled to the output of the conduit 116 and combines the air and water to produce a vaporous mist. A heated screen 140 is positioned in the path of the mist and vaporizes the mist stream, converting the water component to steam. A first thermocouple 142 is provided to monitor the temperature of the screen 140 so that the stream exiting the dispensing head 118 and entering the nasal passages of the user is kept around 110_F. A second thermocouple 144 monitors the temperature of the exiting stream so that the air pump 124 can be controlled to increase or decrease the air flow which would tend to lower or elevate, respectively, the temperature of the steam exiting the dispensing head 118.

In FIG. 7, a controller module 150 is shown in block diagrammatic form. The controller module 150 is connected to receive electrical power from a relatively low voltage power supply 152. Additional inputs are received from the float switch 130 and the first and second thermocouples 142, 144. A user interface 154 provides signal inputs representing user settings for the duration and frequency of the steam pulses and can include alarm indicators to the user.

A timer circuit 156 is controlled by the user interface 154 and provides input to a control circuit 160. Comparator circuits 158 receive inputs from the first and second thermocouples 142, 144 and provide signal outputs to the control circuit 160 when there is a departure from predetermined operating parameters. The control circuit 160 supplies power to the air and liquid pumps 124, 132 and, in response to appropriate signals from the timer 156 and comparator 158 operates the pumps to supply steam increments to the user at the proper temperature and at the desired duration and frequency. The control circuit 160 can also respond to the float switch 130 inputs to generate appropriate alarm signals in the user interface 154 and, if necessary, terminate operation of the entire system should the reservoir become dangerously low in fluid.

The grid 140 temperature is monitored by the thermocouple 142 so that the temperature is stable within predetermined operating limits. Power is applied to the grid 140 in advance of an energizing pulse to the fluid pump 132. The power to the grid 140 is stopped between increments of vapor and reapplied for the next vapor increment. The vapor temperature sensor 144 provides an input to the control circuits 160 so that the air pump 124, fluid pump 132 and grid 140 are all operated to maintain a flow of heated mist at a predetermined temperature over a prescribed interval which parallels the inhalation portion of a breathing cycle.

In operation, at the first symptoms of a cold, the user places the head piece 122 over the head and adjusts the boom 120 so that the dispenser head 118 is adjacent the nostril openings. After measuring the resting breathing rate, the duration of a puff and the interval between puffs can be dialed into the user interface 154. When connected to a source of electrical power, the air pump 124 is energized and the fluid pump 132 is also energized. A first increment of fluid is sent through the system and mixed with air in venturi 138.

The moisture laden air is applied to the grid 140 which was energized to bring its temperature to a level greater than that required to create steam from the moisture Since the "puff" of moist air is being propelled forward by the air pump 124, the "puff" of moist air, converted to steam at the grid 140, continues until it is inhaled during a breathing cycle.

The puff of steam is heated to a temperature above that desired in the nose, but cools as it travels to the interior of the nose and is capable of elevating the temperature of the nasal mucosa to a level that is hostile to the rhinovirus. Subject to further testing and evaluation, the pumps are operated to maintain the exiting stream at the desired temperature. This may necessitate operating both pumps intermittently.

The timing of the generation of the increments of heated, moist vapor is based on the breathing cycle of the user. It is presently contemplated that the generation of the heated vapor should start just prior to the beginning of the inhalation portion of the cycle and terminate before the end of the inhalation portion. No mist is provided through the beginning of the exhalation portion although the generation may begin at or near the end of the exhalation portion. The user controls permit synchronization of the heated moist air with inhalation. It is believed that the absence of heated moist air during exhalation will have no adverse effect and will encourage compliance with a treatment that should extend for the recommended duration of an hour.

Thus there has been shown and described in alternative embodiments, a method and apparatus for providing an elevated temperature environment within the nose. It is believed that subjecting the nasal passages to a moistened atmosphere at a temperature which is hostile to many viruses and bacteria may prevent viral reproduction and which, if done early enough and for a sufficiently long treatment period may prevent the onset of the common cold. If, however, the treatment is too late to prevent the cold, the treatment can be palliative and will help to relieve the discomfort of the cold symptoms.

While the described embodiments have utilized vapor temperatures of 110°, based upon the studies cited, it is believed that raising the temperature of the nasal mucosa to at least 99° F. and maintaining it at that temperature for a sufficiently long time will destroy the viruses. Other modifications and variations will occur to those skilled in the art and the invention should be limited only by the scope of the claims appended hereto.

What is claimed as new is:

1. A method of treating a user for naso-pharyngeal viral attacks comprising the steps of:
   providing a source of moist vapor heated to a temperature between 95-110 degrees F., wherein said temperature is controlled at least in part by sensing a temperature of said moist vapor heated air and controlling an air pump in response to said temperature;
   applying said heated moist vapor to the nasal mucosa of the user;
   interrupting the application of heated moist vapor via an intermittently controlled valve for a prescribed interval determined by a user control so that it is applied primarily during the inhalation portion of a breathing cycle; and
   continuing the application of heated moist vapor for a period in excess of 45 minutes; wherein the application of heated moist vapor is timed to coincide with an inhalation and in which the application is interrupted at the end of the inhalation.

2. The method of claim 1 in which said period is at least one hour.

3. The method of claim 1 in which the application of heated moist vapor is suspended during exhalation.

4. A method of treating a user for naso-pharyngeal viral attacks comprising the steps of:
   providing a source of moist vapor heated to a temperature between 98.6-110 degrees F., wherein said temperature is controlled at least in part by sensing a temperature of said moist vapor heated air and controlling an air pump in response to said temperature;
   applying said heated moist vapor to the nasal mucosa of the user;
   interrupting the application of heated moist vapor via an intermittently controlled valve for a prescribed interval determined by a user control so that it is applied primarily during the inhalation portion of a breathing cycle; and
   continuing the application of heated vapor for a period in excess of 45 minutes; wherein the application of heated moist vapor is timed to coincide with an inhalation and in which the application is interrupted at the end of the inhalation.

5. The method of claim 4 in which said period is at least one hour.

6. The method of claim 4 in which the application of heated moist vapor is suspended during exhalation.

7. A method of treating a user for naso-pharyngeal viral attacks comprising the steps of:
   providing a source of moist vapor heated to a temperature between 98.6-110 degrees F., wherein said temperature is controlled at least in part by sensing a temperature of said moist vapor heated air and controlling an air pump in response to said temperature;
   applying said heated moist vapor to the nasal mucosa of the user;
   interrupting the application of heated moist vapor via an intermittently controlled valve for a prescribed interval determined by a user control so that it is applied primarily during the inhalation portion of a breathing cycle; and
   continuing the application of heated moist vapor for a period in excess of 45 minutes; wherein the application of heated moist vapor is timed to coincide with an inhalation and in which the application is interrupted at the end of the inhalation.

8. The method of claim 7 in which said period is at least one hour.

* * * * *

UNITED STATES PATENT AND TRADEMARK OFFICE
CERTIFICATE OF CORRECTION

PATENT NO. : 7,552,730 B2
APPLICATION NO. : 11/062175
DATED : June 30, 2009
INVENTOR(S) : Lawrence Kates It is certified that error appears in the above-identified patent and that said Letters Patent is hereby corrected as shown below:

On Page 2, Column 2 at line 10, under Other Publications change "4768" to --4766--.

Signed and Sealed this

Twenty-third Day of March, 2010

David J. Kappos
*Director of the United States Patent and Trademark Office*